United States Patent [19]

Yano et al.

[11] Patent Number: 5,475,118
[45] Date of Patent: Dec. 12, 1995

[54] 1-PHENYLPYRROLIDONE DERIVATIVES HAVING OPTICAL ACTIVITY, INTERMEDIATE FOR THE PREPARATION THEREOF AND PROCESSES FOR THEIR PREPARATION

[75] Inventors: Shingo Yano; Tomoyasu Ohno, both of Hannou; Kazuo Ogawa, Myozai; Tetsuhiko Shirasaka, Hannou, all of Japan

[73] Assignee: Taiho Pharmaceutical Co., Ltd., Tokyo, Japan

[21] Appl. No.: 211,950

[22] PCT Filed: Sep. 8, 1993

[86] PCT No.: PCT/JP93/01274

§ 371 Date: May 3, 1994

§ 102(e) Date: May 3, 1994

[87] PCT Pub. No.: WO94/06767

PCT Pub. Date: Mar. 31, 1994

[30] Foreign Application Priority Data

Sep. 11, 1992 [JP] Japan .................................. 4-242887

[51] Int. Cl.⁶ .................. C07D 207/26; A61K 31/40
[52] U.S. Cl. .................................................. 548/551
[58] Field of Search ........................ 548/551; 514/424

[56] References Cited

U.S. PATENT DOCUMENTS 5,145,865  9/1992  Fuji et al. ............................. 514/424

FOREIGN PATENT DOCUMENTS

0393607A3  10/1990  European Pat. Off. .

OTHER PUBLICATIONS

Jacques et al, "Enantiomers, Racemates, and Resolutions", 1991, pp. 263–264.

*Primary Examiner*—David B. Springer
*Attorney, Agent, or Firm*—Nikaido, Marmelstein, Murray & Oram

[57] ABSTRACT

Disclosed are a 1-phenylpyrrolidone derivative having optical activity and represented by the formula (I)

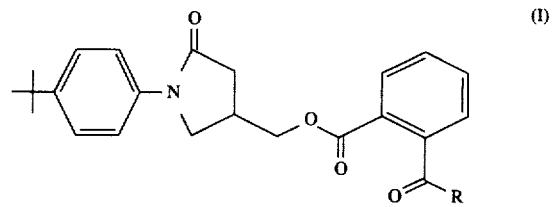

wherein R represents an optionally substituted optically active α-phenylethylamino group, a 1-phenylpyrrolidone derivative represented by the formula (I-a)

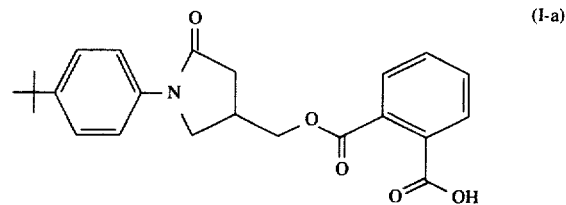

and processes for preparing the 1-phenylpyrrolidone derivatives represented by the formulas (I) and (I-a), respectively.

23 Claims, No Drawings ent 5,475,118

1-PHENYLPYRROLIDONE DERIVATIVES HAVING OPTICAL ACTIVITY, INTERMEDIATE FOR THE PREPARATION THEREOF AND PROCESSES FOR THEIR PREPARATION

FIELD OF THE INVENTION

The present invention relates to a novel 1-phenylpyrrolidone derivative having optical activity, an intermediate for the preparation of the derivative, and processes for their preparation. The compound of the present invention is useful as an intermediate for preparing an optically active form of a compound represented by the following formula (II) which is useful as an agent for treating hyperlipidemia which has an activity to inhibit the synthesis of fatty acids and an activity to inhibit the synthesis of cholesterol

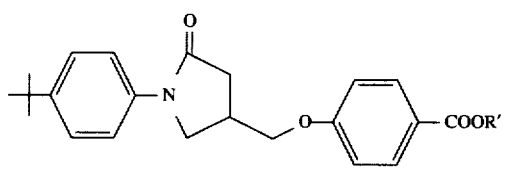

wherein R' is a hydrogen atom or a lower alkyl group such as an alkyl group having 1 to 6 carbon atoms.

BACKGROUND ART

An optically inactive, racemic form of the compound of the formula (II) is disclosed in Japanese Unexamined Patent Publication (Kokai) Hei 3-275666 (European Patent Publication No. 393607), but no report has been made on the synthesis of an optically active form of the compound of the formula (II).

DISCLOSURE OF THE INVENTION

The present inventors conducted extensive research on processes for preparing the optically active form of the compound of the formula (II) and found that a 1-phenylpyrrolidone derivative having optical activity and represented by the formula (I) which is a novel compound undisclosed in literature is useful as an intermediate for preparing the optically active form of the compound of the formula (II). The present inventors completed this invention on the basis of this finding.

The present invention provides a 1-phenylpyrrolidone derivative having optical activity and represented by the formula (I)

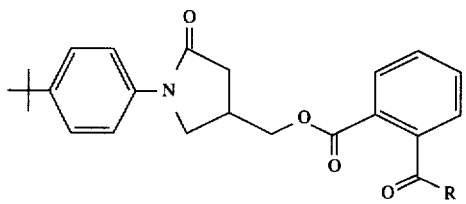

wherein R represents an optionally substituted optically active α-phenylethylamino group.

The present invention also provides a 1-phenylpyrrolidone derivative represented by the formula (I-a)

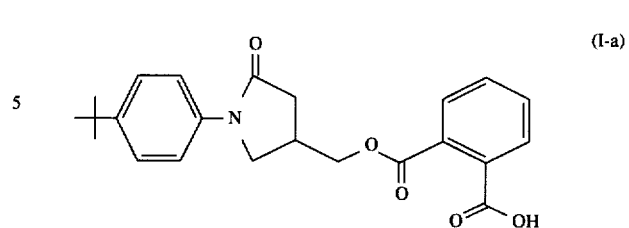

which is an intermediate for preparing the 1-phenylpyrrolidone derivative of the formula (I) having optical activity.

The present invention further provides a process for preparing the foregoing 1-phenylpyrrolidone derivative having optical activity and represented by the formula (I), characterized in that the process comprises the steps of:

i) reacting the foregoing compound of the formula (I-a) with a chlorinating agent in a solvent which does not participate in the reaction to convert the compound to the acid chloride thereof, ii) reacting the acid chloride prepared in the step i) with an optionally substituted optically active α-phenylethylamine in the presence of a basic compound in a solvent which does not participate in the reaction to give a mixture of diastereomers of a compound represented by the formula (I-b)

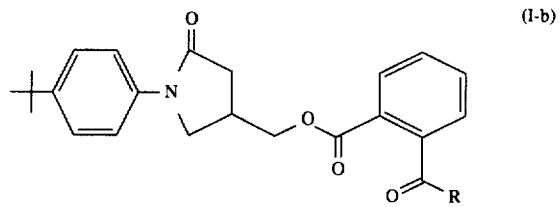

wherein R is as defined above, and iii) optionally conducting resolution of the diastereomer mixture obtained in the step ii) to give an optically active compound represented by the formula (I-b')

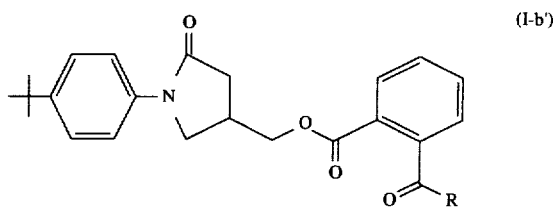

wherein R is as defined above.

The present invention also provides a process for preparing the foregoing compound of the formula (I-a), comprising the step of reacting a racemic mixture represented by the formula (III)

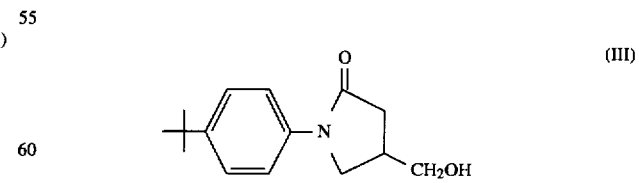

with phthalic anhydride for esterification in the presence of a basic compound in a solvent which does not adversely affect the reaction.

The optically active 1-phenylpyrrolidone derivatives of the formula (I) may exist as four different optical isomers. The present invention includes each of such optically active isomers, and any mixtures of the diastereomers (optically active isomers).

The substituent for the "optionally substituted optically active α-phenylethylamino group" which is represented by R in the invention is one introduced to the o-position, m-position or p-position of the phenyl group of the α-phenylethylamino group. Particularly preferable among them is one introduced to the p-position thereof. Examples of the substituent are a lower alkyl group having 1 to 4 carbon atoms, a halogen atom such as fluorine, chlorine, bromine, iodine, etc., nitro group, and so on. Preferred p-substituted phenyl groups are p-tolyl group, p-bromophenyl group, p-nitrophenyl group, etc.

The optically active 1-phenylpyrrolidone derivative of the formula (I) of the invention (I-b, I-b') can be synthesized in accordance with Reaction Scheme (i) illustrated below from a compound of the formula (III) in the form of racemic mixture via the compound of the formula (I-a) in the form of racemic mixture as the intermediate.

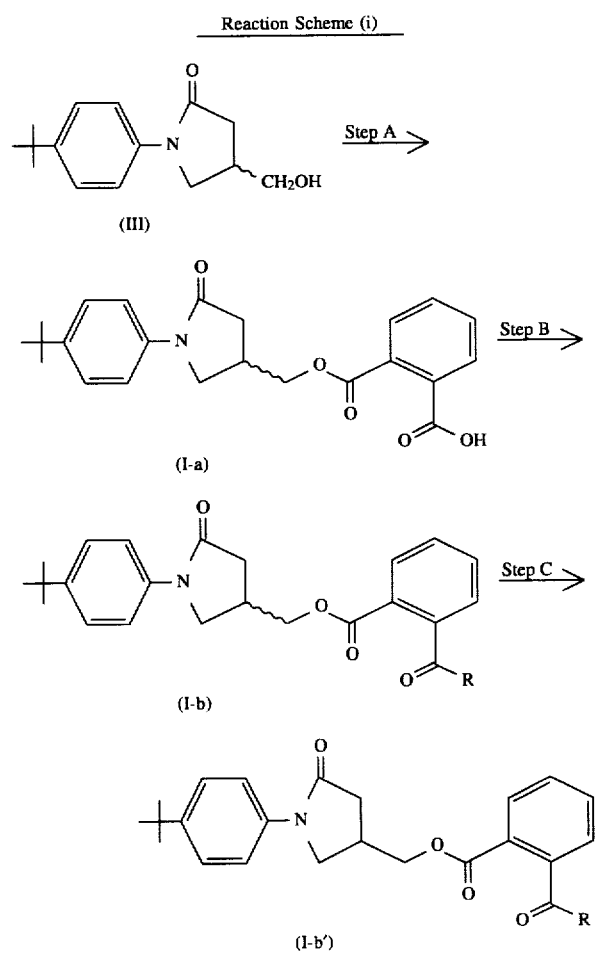

In the formulas, R is as defined above.

In Reaction Scheme (i), the steps are conducted as described below in greater detail.

Step A

The known racemic mixture represented by the formula (III) is reacted with phthalic anhydride (esterification reaction) in a suitable solvent in the presence of a basic compound, giving the compound of the formula (I-a).

Solvents useful for the reaction are not specifically limited insofar as they do not adversely affect the reaction. Examples of useful solvents are ethers such as diethyl ether, tetrahydrofuran, dioxane, etc., halogenated hydrocarbons such as dichloromethane, chloroform, etc., aromatic hydrocarbons such as benzene, toluene, xylene, etc., amines such as pyridine, piperidine, triethylamine, etc., and aprotic polar solvents such as N,N-dimethylformamide, N,N-dimethylacetamide, dimethylsulfoxide, etc. These solvents can be used singly or at least two of them are usable in mixture.

Examples of the basic compound are organic basic compounds such as tertiary amines, e.g. triethylamine, pyridine, etc. and inorganic basic compounds such as sodium hydride, etc. When triethylamine, pyridine or other basic compound is used as a solvent, they can act also as a basic compound, and therefore an additional basic compound is not necessarily used.

As to the proportions of the starting materials to be used in the esterification reaction, about 1 to about 2 moles of phthalic anhydride and about 1 to about 3 moles of the basic compound are used per mole of the compound of the formula (III). The reaction temperature is in the range of approximately 0° C. to the boiling point of the solvent, preferably about 0° to about 80° C. The reaction time is in the range of about 0.5 to about 48 hours, preferably about 2 to about 24 hours.

The compound of the formula (I-a) from the reaction mixture prepared by the foregoing reaction is used as a starting material in the subsequent reaction step after isolation or without isolation.

Step B

The compound of the formula (I-a) prepared in step A is reacted with a chlorinating agent (chlorination reaction) in a suitable solvent to thereby convert the compound to the acid chloride thereof. The acid chloride is then reacted with an optionally substituted optically active α-phenylethylamine in a suitable solvent in the presence of a basic compound, giving the compound of the formula (I-b) in the form of a diastereomer mixture.

Solvents for use in the conversion to the acid chloride are not specifically limited insofar as they do not participate in the reaction. Useful solvents include, for example, halogenated hydrocarbons such as dichloromethane, chloroform, etc. and aromatic hydrocarbons such as benzene, toluene, xylene, etc. These solvents can be used singly or at least two of them are usable in mixture.

Useful chlorinating agents include, for example, thionyl chloride, phosphorus pentachloride, etc.

As to the proportions of the starting materials to be used in the chlorination reaction, about 1 to about 3 moles of the chlorinating agent is used per mole of the compound of the formula (I-a). The reaction temperature is in the range of approximately 0° C. to the boiling point of the solvent, preferably about 10° to about 80° C. The reaction time is in the range of about 0.5 to about 12 hours, preferably about 1 to about 3 hours.

After completion of the chlorination reaction, the solvent alone or the solvent and the excess chlorinating agent is (are) evaporated off whereby the acid chloride of the compound of the formula (I-a) can be quantitatively obtained.

Next, the obtained acid chloride is reacted with an optionally substituted optically active α-phenylethylamine (reaction for the introduction of α-phenylethylamine).

The optionally substituted optically active α-phenylethylamine which is used in this reaction is a compound represented by the formula (IV)

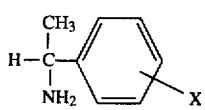

(IV)

wherein X is a hydrogen atom, a lower alkyl group having 1 to 4 carbon atoms, a halogen atom or nitro group. Examples of such compounds are (S)-(−)-α-phenylethylamine, (S)-(−)-4-methyl-α-phenylethylamine, (S)-(−)-4-bromo-α-phenylethylamine, (S)-(−)-4-nitro-α-phenylethylamine, (R)-(+)-α-phenylethylamine, (R)-(+)-4-methyl-α-phenylethylamine, (R)-(+)-4-bromo-α-phenylethylamine or (R)-(+)-4-nitro-α-phenylethylamine, etc. These compounds of the formula (IV), which are all known compounds, are readily available or can be synthesized according to known processes.

Solvents which can be used in the reaction for the introduction of α-phenylethylamine are not specifically limited insofar as they do not participate in the reaction. Useful solvents include, for example, halogenated hydrocarbons such as dichloromethane, chloroform, etc., and aprotic polar solvents such as N,N-dimethylformamide, N,N-dimethylacetamide, dimethylsulfoxide, etc. These solvents can be used singly or at least two of them are usable in mixture.

Examples of the basic compound are organic basic compounds such as tertiary amines, e.g. triethylamine, pyridine, etc.

As to the proportions of the starting materials to be used in the reaction for the introduction of α-phenylethylamine, about 1 to about 2 moles of the optionally substituted optically active α-phenylethylamine, and about 1 to about 5 moles of the basic compound are used per mole of the acid chloride. The reaction temperature is in the range of approximately 0° C. to the boiling point of the solvent, preferably about 0° to about 80° C. The reaction time is in the range of about 0.5 to about 12 hours, preferably about 1 to about 3 hours.

The diastereomer mixture represented by the formula (I-b) can be easily isolated and purified by conventional separation methods such as silica gel column chromatography, extraction, etc. from the reaction mixture obtained by the foregoing reaction.

Step C

An optically active compound of the formula (I-b') can be prepared from the diastereomer mixture represented by the formula (I-b) by conventional methods such as fractional recrystallization using a suitable solvent, e.g. ethyl acetate, methanol, hexane-ethyl acetate mixture, silica gel column chromatography etc.

The optically active form of the compound of the formula (II) can be synthesized from the compound of the formula (I-b') of the present invention according to Reaction Scheme (ii) illustrated below.

Reaction Scheme (ii)

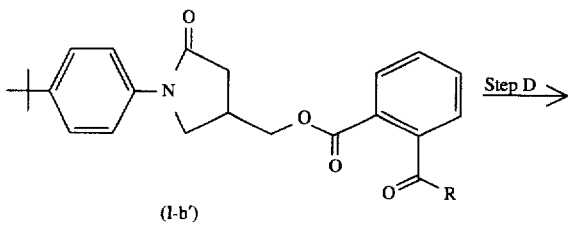

(I-b')

Step D

-continued
Reaction Scheme (ii)

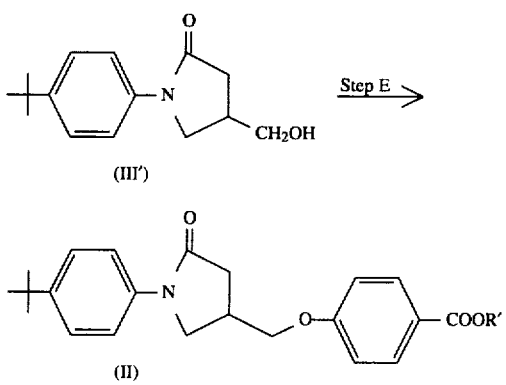

In the above formulas, R' and R are as defined above.

In Reaction Scheme (ii), the steps are conducted as described below in greater detail.

Step D

An optically active form of the compound of the formula (III') can be produced by hydrolyzing in the presence of an alkali a (+)- form or (−)- form of the compound of the formula (I-b') prepared in Reaction Scheme (i).

Useful alkalis include, for example, hydroxides of alkali metals such as sodium hydroxide, potassium hydroxide, etc. Useful solvents include, for example, alcohols such as methanol, ethanol and isopropanol, water, etc.

As to the proportions of the starting materials to be used in the hydrolysis reaction, about 1 to about 2 moles of the alkali is used per mole of the compound of the formula (I-b'). The reaction temperature is in the range of approximately 0° C. to the boiling point of the solvent, preferably about 0° to about 80° C. The reaction time is in the range of about 0.2 to about 12 hours, preferably about 0.5 to about 3 hours.

Step E

The compound of the formula (II) having optical activity can be prepared from the compound of the formula (III') obtained in step D by following the same procedure as the method disclosed in Japanese Unexamined Patent Publication (Kokai) No. Hei 3-275666 (European Patent Publication No.393607). The details of the synthesis of the compound of the formula (II) will be given in Reference Examples to be described later.

Conventional process for preparing the compound (racemate) of the formula (II) is intended to produce the compound of the formula (II) directly from the compound (racemate) of the formula (III). On the other hand, an attempt may be made to subject the compound (racemate) of the formula (II) directly to optical resolution in order to obtain the compound of the formula (II) having an optical activity. However, it is very difficult to achieve the optical resolution of the compound (racemate) of the formula (II) without resort to the techniques of the present invention. Contrastedly, the compound of the formula (II) having optical activity can be easily produced from the compound of the formula (I-b) of the present invention (diastereomer mixture) via the compound of the formula (I-b') having optical activity.

Effects of the Invention

When the 1-phenylpyrrolidone derivative of the formula (I) of the present invention having optical activity is used as an intermediate, 4-[1-(4-t-butylphenyl)-2-pyrrolidone-4-yl] methoxybenzoic acid or a lower alkyl ester thereof of the formula (II) which is useful as an agent for treating hyperlipidemia can be easily produced by using known method.

That is to say, the compound of the formula (I-b) of the present invention, which is prepared by reacting the intermediate compound (I-a) of the present invention with an optionally substituted optically active α-phenylethylamine, can be easily resolved into isomers, and therefore the compound (I-b') of the present invention having optical activity can be easily recovered. Using the compound (I-b') of the present invention having optical activity as the starting material, an optically active form of 4-[1-(4-t-butylphenyl)-2-pyrrolidone-4-yl]methoxybenzoic acid or a lower alkyl ester thereof of the formula (II) can be easily prepared by utilizing the known methods.

An optically active compound of the formula (II) has a higher absorption and a higher therapeutic effect and involves less side effects than a racemic form.

EXAMPLES

Examples and Reference Examples are given below to illustrate the present invention in detail.

EXAMPLE 1

Synthesis of phthalic acid mono-[1-(4-t-butylphenyl)-2-pyrrolidone-4-yl]methyl ester (I-a)

A 8.3 ml (60 mmol) quantity of triethylamine was added to a solution of 12.35 g (50 mmol) of [1-(4-t-butylphenyl)-2-pyrrolidone-4-yl)methyl alcohol (III) and 7.4 g (50 mmol) of phthalic anhydride in dichloromethane (150 ml), and the mixture was refluxed with heating for 24 hours. The reaction mixture was washed with a dilute hydrochloric acid, dried over magnesium sulfate and concentrated under reduced pressure to give 19.8 g (quantitative yield) of the title compound.

Melting point: 155° C.–157° C.

NMR spectrum (CDCl$_3$) δ

2.66 (1H, dd, J=16.8, 6.3 Hz), 2.8–3.0 (2H, m), 3.72 (1H, dd, J=9.9, 5.3 Hz), 3.99(1H, dd, J=9.9, 8.0 Hz ), 4.39 ( 2H, d, J=6.0Hz ), 7.33 ( 2H, d, J=8.9Hz ), 7.46 (2H, d, J=8.9Hz), 7.50–7.60 (2H, m), 7.65–7.73 (2H, m), 7.84–7.90 (2H, m)

MASS spectrum (FAB) 394 (M$^+$−1)

EXAMPLE 2

Synthesis of (−)-2-[(S)-1-(4-t-butylphenyl)-2-pyrrolidone-4-yl]methoxycarbonyl benzoic acid (S)-α-phenylethylamide (I-b')

A benzene (100 ml) solution of 19.8 g (50 mmol) of phthalic acid mono-[1-(4-t-butylphenyl)-2-pyrrolidone-4-yl]methyl ester obtained in Example 1 and 7.3 ml (0.1 mol) of thionyl chloride was refluxed with heating for 2 hours. The reaction mixture was concentrated under reduced pressure and 100 ml of dichloromethane was added thereto. To the mixture was added dropwise a solution of 6.05 g (50 mmol) of (S)-(−)-a-phenylethylamine and 10.4 ml (75 mmol) of triethylamine in dichloromethane (50 ml) over a period of 10 minutes with ice-cooling, and the resulting mixture was stirred at the room temperature for 1.5 hours.

The reaction mixture was concentrated under reduced pressure and 100 ml of ethyl acetate was added thereto. The mixture was washed with a dilute hydrochloric acid and with water, dried over magnesium sulfate and filtered. The filtrate was concentrated under reduced pressure. The residue was subjected to silica gel column chromatography and purified by chloroform-ethyl acetate gradient elution to give 17.93 g of a diastereomer mixture (I-b) of the title compound as an oil (yield 72%).

Further, hexane-ethyl acetate mixed solvent was added to the mixture for crystallization, and recrystallization from ethyl acetate was conducted twice. Thus, 5.5 g of the title compound as one of the diastereomers was obtained (>99% d.e. (diastereomer excess)).

Melting point: 184° C.–186° C.

Specific rotation: $[\alpha]_D^{25}$=−33.0°(c=1.0, $CH_2Cl_2$)

NMR spectrum (CDCl$_3$)δ

1.59 (3H, d, J=6.9Hz), 2.27–2.41 (1H, m), 2.55–2.71 (2H, m), 3.68 (1H, dd, J=10.2, 5.3 Hz), 3.92 (1H, dd, J=10.2, 7.9 Hz), 4.18–4.31 (2H, m), 5.29 (1H, dq, J=7.9, 7.0 Hz), 6.11 (1H, d, J=7.9Hz), 7.25–7.88 (13H, m)

MASS spectrum (EI)498 (M$^+$)

Elementary analysis (for $C_{31}H_{34}N_2O_4$)

|  | C | H | N |
|---|---|---|---|
| Calculated | 74.67 | 6.87 | 5.62 |
| Found | 74.76 | 6.94 | 5.52 |

EXAMPLE 3

Synthesis of (+)-2-[(R)-1-(4-t-butylphenyl)-2-pyrrolidone-4-yl]methoxycarbonylbenzoic acid (R)-α-phenylethylamide (I-b')

A reaction was conducted in the same manner as in Example 2 except that (R)-(+)-α-phenylethylamine was used in place of (S)-(−)-α-phenylethylamine to give a diastereomer mixture (I-b) of the title compound (yield 68%).

Further, a hexane-ethyl acetate mixed solvent was added to the mixture for crystallization, and recrystallization from methanol was conducted twice. Thus, the title compound as one of the diastereomers was obtained (>99% d.e.).

Melting point: 186° C.–187° C.

Specific rotation: $[\alpha]_D^{25}$=+32 4° (c=1.0, $CH_2Cl_2$)

NMR spectrum (CDCl$_3$) δ

1.59 (3H, d, J=6.9Hz), 2.27–2.41 (1H, m), 2.55–2.71 (2H, m), 3.68 (1H, dd, J=10.2, 5.3 Hz), 3.92 (1H, dd, J=10.2, 7.9 Hz), 4.18–4.31 (2H, m), 5.29(1H, dq, J=7.9, 7.0 Hz), 6.11 (1H, d, J=7.9Hz), 7.25–7.88 (13H, m)

MASS spectrum (EI)498(M$^+$)

Elementary analysis (for $C_{31}H_{34}N_2O_4$)

|  | C | H | N |
|---|---|---|---|
| Calculated | 74.67 | 6.87 | 5.62 |
| Found | 74.73 | 7.06 | 5.60 |

REFERENCE EXAMPLE 1

Synthesis of (S)-(−)-[1-(4-t-butylphenyl)-2-pyrrolidone-4-yl]methyl alcohol (III')

A 4% aqueous solution of sodium hydroxide (18 ml) was added dropwise at 60° C. to a suspension of 4.47 g (8.98 mmol) of (−)-2-[(S)-1-(4-t-butylphenyl)-2-pyrrolidone-4-yl]

methoxycarbonylbenzoic acid (S)-α-phenylethylamide (I-b') obtained in Example 2 in 35 ml of ethanol, and the mixture was stirred for 30 minutes.

The reaction mixture was concentrated under reduced pressure and extracted with ether twice. The extract was washed with water, with a dilute hydrochloric acid and with water, dried over magnesium sulfate and filtered. The filtrate was concentrated under reduced pressure to give 2.12 g of the title compound (yield 96%, >99% e.e.(enantiomer excess)).

Melting point: 83° C.–84° C.
Specific rotation: $[\alpha]_D^{25}=-10.8°$ (c=1.0, $CH_2Cl_2$)
Elementary analysis (for $C_{15}H_{21}NO_2$)

|  | C | H | N |
|---|---|---|---|
| Calculated | 72.84 | 8.56 | 5.66 |
| Found | 72.91 | 9.02 | 5.47 |

REFERENCE EXAMPLE 2

Synthesis of (R)-(+)-[1-(4-t-butylphenyl)-2-pyrrolidone-4-yl]methyl alcohol (III')

A reaction was conducted in the same manner as in Reference Example 1 except that (+)-2-[(R)-1-(4-t-butylphenyl)-2-pyrrolidone-4-yl] methoxycarbonylbenzoic acid (R)-α-phenylethylamide obtained in Example 3 was used in place of (–)-2-[(S)-1-(4-t-butylphenyl)-2-pyrrolidone-4-yl] methoxycarbonylbenzoic acid (S)-α-phenylethylamide to give the title compound (yield 96%, >99% e.e.).

Melting point: 83° C.–84° C.
Specific rotation: $[\alpha]_D^{25}=+9.9°$ (c=1.0, $CH_2Cl_2$)
Elementary analysis (for $C_{15}H_{21}NO_2$)

|  | C | H | N |
|---|---|---|---|
| Calculated | 72.84 | 8.56 | 5.66 |
| Found | 72.91 | 8.92 | 5.50 |

REFERENCE EXAMPLE 3

Synthesis of (R)-(–)-[1-(4-t-butylphenyl)-2-pyrrolidone-4-yl]methyl methanesulfonate A 0.83 ml (1.08 mmol) quantity of methanesulfonyl chloride was added dropwise with ice-cooling to a solution of 2.42 g (9.80 mmol) of (R)-(+)-[1-(4-t-butylphenyl)-2-pyrrolidone-4-yl]methyl alcohol (III') obtained in Reference Example 2 and 1.5 ml (1.08 mmol) of triethylamine in dichloromethane (20 ml), and the mixture was stirred at the room temperature for 30 minutes.

The reaction mixture was diluted with ethyl acetate, washed with an aqueous solution of ammonium chloride and with an aqueous solution of sodium chloride, dried over magnesium sulfate and filtered. The filtrate was concentrated under reduced pressure to give 3.12 g of the title compound (yield 98%).

Melting point: 108° C.–109° C.
Specific rotation: $[\alpha]_D^{25}=-1.7°$ (c=1.0, $CH_2Cl_2$)
Elementary analysis (for $C_{16}H_{23}NO_4S$)

|  | C | H | N |
|---|---|---|---|
| Calculated | 59.05 | 7.12 | 4.30 |
| Found | 58.62 | 7.34 | 4.44 |

REFERENCE EXAMPLE 4

Synthesis of (S)-(+)-[1-(4-t-butylphenyl)-2-pyrrolidone-4-yl]methyl methanesulfonate A reaction was conducted in the same manner as in Reference Example 3 except that (S)-(–)-[1-(4-t-butylphenyl)-2-pyrrolidone-4-yl]methyl alcohol (III') obtained in Reference Example 1 was used in place of (R)-(+)-[1-(4-t-butylphenyl)-2-pyrrolidone-4-yl] methyl alcohol to give the title compound (yield 99%).

Melting point: 108° C.–109° C.
Specific rotation: $[\alpha]_D^{25}=+2.0°$ (c=1.0, $CH_2Cl_2$)
Elementary analysis (for $C_{16}H_{23}NO_4S$)

|  | C | H | N |
|---|---|---|---|
| Calculated | 59.05 | 7.12 | 4.30 |
| Found | 58.64 | 7.38 | 4.38 |

REFERENCE EXAMPLE 5

Synthesis of methyl (R)-(–)-4-[1-(4-t-butylphenyl)-2-pyrrolidone-4-yl]methoxybenzoate (II)

A suspension of 3.0 g (9.23 mmol) of (R)-(–)-[1-(4-t-butylphenyl)-2-pyrrolidone-4-yl]methyl methanesulfonate, 1.4 g (9.23 mmol) of methyl p-hydroxybenzoate and 1.53 g (11.1 mmol) of potassium carbonate in 30 ml of N,N-dimethylformamide was stirred at 70° C. for 15 hours.

The reaction mixture was concentrated under reduced pressure and extracted with ethyl acetate. The extract was washed with water and with an aqueous solution of sodium chloride, dried over magnesium sulfate and filtered. The filtrate was concentrated under reduced pressure and recrystallized from methanol to give 2.68 g of the title compound (yield 72%, >99% e.e.).

Melting point: 126° C.–128° C.
Specific rotation: $[\alpha]_D^{25}=-18.1°$ (c=1.0, $CH_2Cl_2$)
MASS spectrum (FAB) 382 ($M^+$+1)
Elementary analysis (for $C_{23}H_{27}NO_4$)

|  | C | H | N |
|---|---|---|---|
| Calculated | 72.42 | 7.13 | 3.67 |
| Found | 72.49 | 7.30 | 3.64 |

REFERENCE EXAMPLE 6

Synthesis of methyl (S)-(+)-4-[1-(4-t-butylphenyl)-2-pyrrolidone-4-yl] methoxybenzoate (II)

A reaction was conducted in the same manner as in Reference Example 5 except that (S)-(+)-[1-(4-t-butylphenyl)-2-pyrrolidone-4-yl]methyl methanesulfonate obtained in Reference Example 4 was used in place of (R)-(−)-[1-(4-t-butylphenyl)-2-pyrrolidone-4-yl] methyl methanesulfonate to give the title compound (yield 67%, >99% e.e.).

Melting point: 130° C.–131° C.

Specific rotation: $[\alpha]_D^{25}=+16.4°$ (c=1.0, CH$_2$Cl$_2$)

MASS spectrum (FAB)382(M$^+$+1)

Elementary analysis (for C$_{23}$H$_{27}$NO$_4$)

|  | C | H | N |
|---|---|---|---|
| Calculated | 72.42 | 7.13 | 3.67 |
| Found | 72.49 | 7.39 | 3.70 |

REFERENCE EXAMPLE 7

Synthesis of (R)-(−)-4-[1-(4-t-butylphenyl)-2-pyrrolidone-4-yl]methoxybenzoic acid (II)

A 5.7 ml quantity of an 8% aqueous solution of sodium hydroxide was added dropwise at 60° C. to a suspension of 2.18 g (5.72 mmol) of methyl (R)-(−)-4-[1(4-t-butylphenyl)-2-pyrrolidone-4-yl] methoxybenzoate obtained in Reference Example 5 in 55 ml of ethanol, and the mixture was stirred for 16 hours.

The reaction mixture was concentrated under reduced pressure, and a dilute hydrochloric acid was added thereto and the crystals precipitated were collected by filtration. Thus, 2.04 g of the title compound was obtained (yield 97%, >99% e.e.).

Melting point: 247° C.–248° C.

Specific rotation: $[\alpha]_D^{25}=-27.9°$ (c=1.0, DMF)

MASS spectrum (FAB)366(M$^+$−1)

Elementary analysis (for C$_{22}$H$_{25}$NO$_4$)

|  | C | H | N |
|---|---|---|---|
| Calculated | 71.91 | 6.86 | 3.81 |
| Found | 71.92 | 6.94 | 3.65 |

REFERENCE EXAMPLE 8

Synthesis of (S)-(+)-4-[1-(4-t-butylphenyl)-2-pyrrolidone-4-yl]methoxybenzoic acid (II)

A reaction was conducted in the same manner as in Reference Example 7 except that methyl (S)-(+)-4-[1(4-t-butylphenyl)-2-pyrrolidone-4-yl] methoxybenzoate (II) obtained in Reference Example 6 was used in place of methyl (R)-(−)-4-[1-(4-t-butylphenyl)-2-pyrrolidone-4-yl] methoxybenzoate to obtain the title compound (yield 98%, >99% e.e.).

Melting point: 247° C.–248° C.

Specific rotation: $[\alpha]_D^{25}=+27.0°$ (c=1.0, DMF)

MASS spectrum (FAB) 366 (M$^+$−1)

Elementary analysis (for C$_{22}$H$_{25}$NO$_4$)

|  | C | H | N |
|---|---|---|---|
| Calculated | 71.91 | 6.86 | 3.81 |
| Found | 71.76 | 6.93 | 3.60 |

We claim:

1. A 1-phenylpyrrolidone derivative having optical activity and represented by the formula (I)

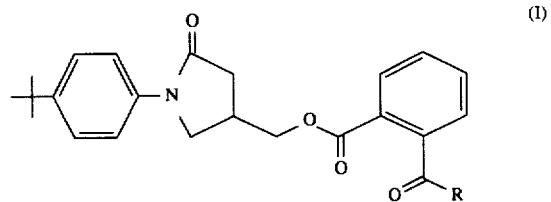

(I)

wherein R represents an optionally substituted optically active α-phenylethylamino group.

2. A 1-phenylpyrrolidone derivative having optical activity according to claim 1 wherein R is an optically active group represented by the formula

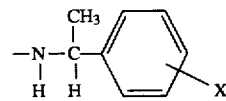

wherein X is a hydrogen atom, a lower alkyl group having 1 to 4 carbon atoms, a halogen atom or nitro group.

3. A 1-phenylpyrrolidone derivative having optical activity according to claim 1 wherein R is an optically active group represented by the formula

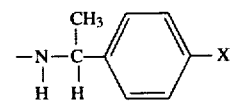

wherein X is a hydrogen atom, a lower alkyl group having 1 to 4 carbon atoms, a halogen atom or nitro group.

4. A 1-phenylpyrrolidone derivative having optical activity according to claim 2 wherein X is a hydrogen atom, methyl group, a bromine atom or nitro group.

5. A 1-phenylpyrrolidone derivative having optical activity according to claim 2 wherein X is a hydrogen atom.

6. A 1-phenylpyrrolidone derivative represented by the formula (I-a)

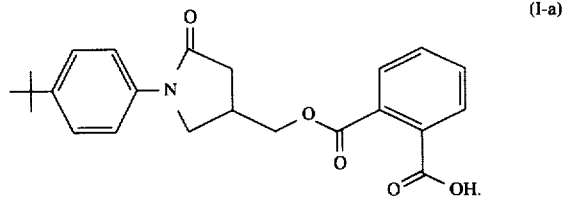

(I-a)

7. A process for preparing a 1-phenylpyrrolidone derivative having optical activity and represented by the formula (I)

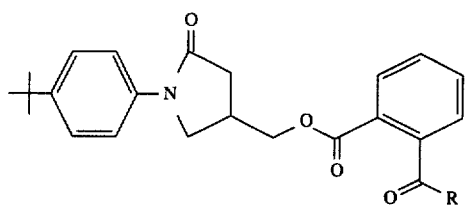

(I)

wherein R represents an optionally substituted optically active α-phenylethylamino group, characterized in that the process comprises the steps of:

a) reacting a compound represented by the formula (I-a)

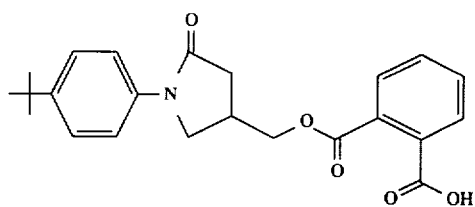

(I-a)

with a chlorinating agent in a solvent which does not participate in the reaction to convert the compound to the acid chloride thereof, b) reacting the acid chloride prepared in step i) with an optionally substituted optically active α-phenylethylamine in the presence of a basic compound in a solvent which does not participate in the reaction to give a mixture of diastereomers of a compound represented by the formula (I-b)

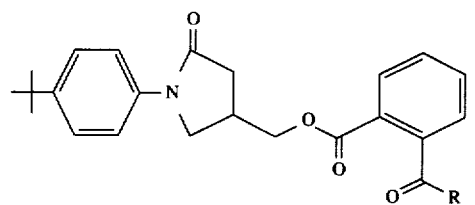

(I-b)

wherein R is as defined above, and c) optionally conducting resolution of the diastereomer mixture obtained in step ii) to give an optically active compound represented by the formula (I-b')

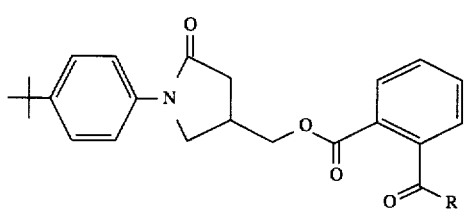

(I-b')

wherein R is as defined above.

8. A process for preparing the 1-phenylpyrrolidone derivative according to claim 7 wherein the chlorinating agent which is used in step i) is thionyl chloride or phosphorus pentachloride.

9. A process for preparing the 1-phenylpyrrolidone derivative according to claim 7 wherein the solvent which does not participate in the reaction and which is used in step i) is at least one solvent selected from the group consisting of dichloromethane, chloroform, benzene, toluene and xylene.

10. A process for preparing the 1-phenylpyrrolidone derivative according to claim 7 wherein the optionally substituted optically active α-phenylethylamine which is used in step ii) is a compound represented by the formula (IV)

(IV)

wherein X is a hydrogen atom, a lower alkyl group having 1 to 4 carbon atoms, a halogen atom or nitro group.

11. A process for preparing the 1-phenylpyrrolidone derivative according to claim 7 wherein the optionally substituted optically active α-phenylethylamine which is used in step ii) is a compound represented by the formula

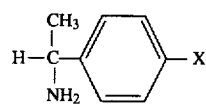

wherein X is a hydrogen atom, a lower alkyl group having 1 to 4 carbon atoms, a halogen atom or nitro group.

12. A process for preparing the 1-phenylpyrrolidone derivative according to claim 7 wherein the basic compound which is used in step ii) is triethylamine or pyridine.

13. A process for preparing a compound represented by the formula (I-a)

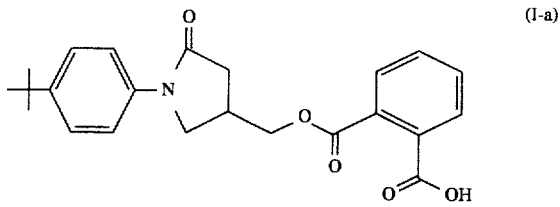

(I-a)

comprising the step of react a racemic mixture represented by the formula (III)

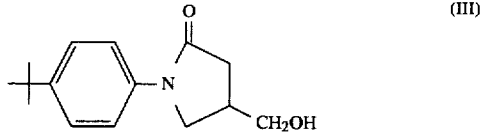

(III)

with phthalic anhydride for esterification in the presence of a basic compound in a solvent which does not adversely affect the reaction.

14. A process for preparing the 1-phenylpyrrolidone derivative according to claim 13 wherein the basic compound is at least one compound selected from the group consisting of triethylamine, pyridine and sodium hydride.

15. A process for preparing the 1-phenylpyrrolidone derivative according to claim 13 wherein the solvent which does not adversely affect the reaction is at least one solvent selected from the group consisting of diethyl ether, tetrahydrofuran, dioxane, dichloromethane, chloroform, benzene, toluene, xylene, pyridine, piperidine, triethylamine, N,N-dimethylformamide, N,N-dimethylacetamide and dimethylsulfoxide.

16. A process for preparing the 1-phenylpyrrolidone derivative according to claim 13 wherein the reaction temperature is in the range of 0° to 80° C.

17. A process for preparing an optically active 1-phenylpyrrolidone derivative of the formula (I):

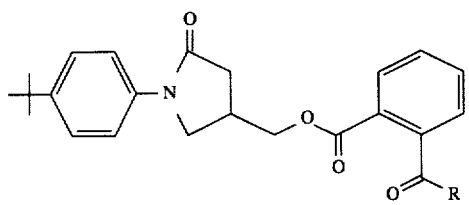

wherein R is a substituted or unsubstituted optically active α-phenylethylamino group, comprising the steps of:

a) esterifying a racemic mixture of the formula (III):

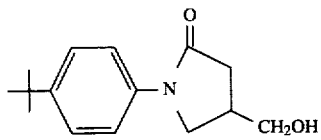

with phthalic anhydride in the presence of a basic compound in a solvent which does not adversely affect the reaction to produce a compound of the formula (I-a):

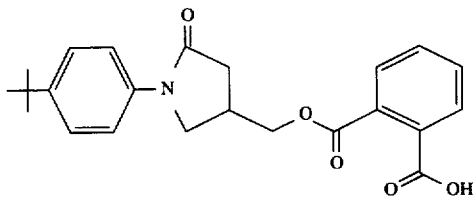

b) reacting the compound of formula (I-a) produced in step a) with a chlorinating agent in a solvent which does not participate in the reaction, to produce the acid chloride of compound (I-a), and c) reacting the acid chloride produced in step b) with a substituted or unsubstituted optically active α-phenylethylamine in the presence of a basic compound in a solvent which does not participate in the reaction, to produce a mixture of diastereomers of the compound of formula (I).

18. The process according to claim 17, further comprising resolving said mixture of diastereomers obtained in step c) to produce an optically active compound of the formula (I), wherein R is a substituted or unsubstituted optically active α-phenylethylamino group.

19. (S)-(+)-4-[1-(4-t-Butylphenyl)-2-pyrrolidone-4-yl]methoxybenzoic acid, or a lower alkyl ester thereof, represented by the formula (II)

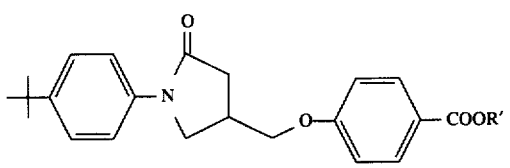

wherein R' is a hydrogen atom or a lower alkyl group.

20. Methyl (S)-(+)-4-[1-(4-t-butylphenyl)-2-pyrrolidone-4-yl]methoxybenzoate.

21. (S)-(+)-4-[1-(4-t-Butylphenyl)-2-pyrrolidone-4-yl]methoxybenzoic acid.

22. A pharmaceutical composition for treating hyperlipidemia comprising as an active ingredient (S)-4-[1-(4-t-butylphenyl)-2-pyrrolidone-4-yl]methoxybenzoic acid, or a lower alkyl ester thereof according to claim 19 in combination with a pharmaceutically acceptable carrier.

23. A method for treating hyperlipidemia in a patient comprising administering (S)-4-[1-(4-t-butylphenyl)-2-pyrrolidone-4-yl]methoxybenzoic acid, or a lower alkyl ester thereof, represented by the formula (II)

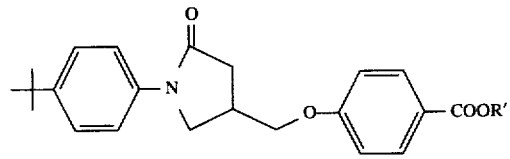

wherein R' is a hydrogen atom or a lower alkyl group.

* * * * *

UNITED STATES PATENT AND TRADEMARK OFFICE
CERTIFICATE OF CORRECTION

PATENT NO. : 5,475,118
DATED : December 12, 1995
INVENTOR(S) : YANO et al.

It is certified that error appears in the above-indentified patent and that said Letters Patent is hereby corrected as shown below:

Column 16,

Claim 22, line 25, delete "(S)-4-[1-(4-t-butylphenyl)-2-pyrrolidone-4-yl] methoxybenzoic acid" insert therefor -- (S)-(+)-4-[1-(4-t-butylphenyl)-2-pyrrolidone-4-yl] methoxybenzoic acid, --

Claim 23, line 30, delete "(S)-4-[1-(4-t-butylphenyl)-2-pyrrolidone-4-yl] methoxybenzoic acid" insert therefor -- (S)-(+)-4-[1-(4-t-butylphenyl)-2-pyrrolidone-4-yl] methoxybenzoic acid, --

Signed and Sealed this

Fifteenth Day of July, 1997

Attest:

BRUCE LEHMAN

*Attesting Officer*      *Commissioner of Patents and Trademarks*